United States Patent [19]

Sollott et al.

[11] 4,268,696

[45] May 19, 1981

[54] METHOD FOR PREPARING HEXANITROSTILBENE

[75] Inventors: Gilbert P. Sollott, Plymouth Meeting, Pa.; Everett E. Gilbert, Morristown; Maurice Warman, Netcong, both of N.J.

[73] Assignee: The United States of America as represented by the Secretary of the Army, Washington, D.C.

[21] Appl. No.: 111,754

[22] Filed: Jan. 14, 1980

[51] Int. Cl.³ .............................................. C07C 79/10
[52] U.S. Cl. ................................................... 568/931
[58] Field of Search ......................................... 568/931

[56] References Cited

U.S. PATENT DOCUMENTS

| | | | |
|---|---|---|---|
| 3,201,481 | 8/1965 | Catino et al. | 568/931 X |
| 3,505,413 | 4/1970 | Shipp | 568/931 |
| 3,699,176 | 10/1972 | Syrop | 568/931 |
| 4,085,152 | 4/1978 | Salter et al. | 568/931 |

FOREIGN PATENT DOCUMENTS 2256144  7/1975  France .................... 568/931

*Primary Examiner*—Leland A. Sebastian
*Attorney, Agent, or Firm*—Nathan Edelberg; Robert P. Gibson; A. Victor Erkkila

[57] ABSTRACT

2,2',4,4',6,6'-hexanitrostilbene, a thermally stable explosive material, is prepared by reacting 2,2',4,4',6,6'-hexanitrobibenzyl with a quinone in a suitable reaction solvent such as hexamethyl phosphoric triamide, dimethyl sulfoxide and N-methyl-pyrrolidinone. The use of organic bases to promote the reaction and to allow the use of normally inoperative reaction solvents is also disclosed.

10 Claims, No Drawings

METHOD FOR PREPARING HEXANITROSTILBENE

GOVERNMENTAL INTEREST

The invention described herein may be manufactured, used, and licensed by or for the Government for Governmental purposes without the payment to us of any royalties thereon.

BACKGROUND OF THE INVENTION

The present invention relates generally to a novel method for preparing 2,2′,4,4′,6,6′-hexanitrostilbene (HNS), an important thermally stable explosive material which is also useful as a nucleant for promoting optimum trinitrotoluene-crystallization.

The discovery and an early synthesis for preparing HNS is disclosed in U.S. Pat. No. 3,505,413 to K. Shipp. That reference teaches adding 2,4,6-trinitrotoluene (TNT) dissolved in an appropriate solvent to a metal hypochlorite solution to form trinitrobenzychloride (TNBCl), which will then react with the metal hydroxide normally present in the hypochlorite solution to form HNS. The reaction can be controlled by drowning the reaction mixture with an acid such as HCl during the TNBCl transition stage to obtain TNBCl and then reacting the TNBCl with a metal hydroxide such as NaOH to form HNS.

This reference also discloses a method for preparing 2,2′,4,4′,6,6′-hexanitrobibenzyl (HNB), a starting material necessary in the instant process, which will be more fully explained below.

Unlike the Shipp process, the instant method for preparing HNS involves the reaction of HNB and a quinone in a suitable solvent. This type of reaction can best be described as dehydrogenation by a quinone and is discussed by H. O. House in *Modern Synthetic Reaction*, 2nd Edition, 1972, W. A. Benjamin, Menlo Park, California, pp 37–44. However, the instant process operates under conditions different from those set forth by House. For example, House states that operative solvents include xylene and orthodichlorobenzene. However, as will be seen below these solvents do not work in the instant method whereas other solvents not previously disclosed for this type synthesis work quite well. Also, the quinones previously found operative with this type synthesis were those containing chlorine or cyano and chlorine groups. However, it has been discovered that benzoquinone, naphthoquinone and others also work while anthraquinone does not.

SUMMARY OF THE INVENTION

An object of the instant invention is to provide a method for producing HNS from HNB.

Another object of the instant invention is to provide a method for promoting the process for producing HNS by reaction of HNB with a quinone.

Yet another object of the instant invention is to be able to use normally inoperative reaction solvents in the process by adding pyridine or other suitable bases to the reaction mixture.

These and other objects that will be made apparent in the detailed description to follow are accomplished by reaction HNB and a quinone in a suitable solvent according to the following reaction scheme, wherein the quinone is illustrated by p-benzoquinone:

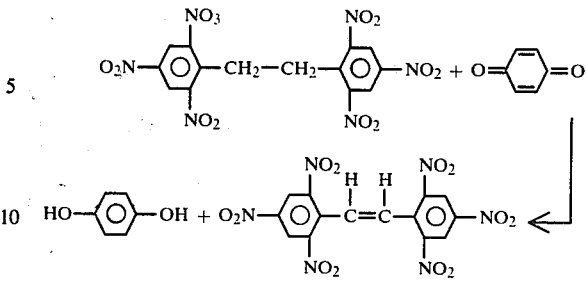

DETAILED DESCRIPTION OF THE INVENTION

As explained previously, the primary starting material is HNB, which can be prepared in accordance with the process set forth in Shipp U.S. Pat. No. 3,505,413. The process entails adding a dilute hypochlorite aqueous solution, to which has been added a small amount of sodium hydroxide, to a solution of trinitrotoluene. Yields of about 79% of the theoretical yield have been obtained. Of course, other processes can be used to obtain HNB as will be readily apparent to those skilled in the art.

Quinones useful in the present process are those which have an oxidation-reduction potential ($E^o$) of at least 0.4 volt to about 1 volt, and preferably in the range of from about 0.7 volt to about 1.0 volt, as determined according to J. B. Conant, and L. F. Fieser, J. Am. Chem. Soc. 45, 2194 (1923); 46, 1858 (1924). Suitable quinones include o- and p- benzoquinones, and 1,2- and 1,4-napthoquinones, which are unsubstituted or substituted by one or more radicals selected from the group consisting of methyl, phenyl, cyano and halogen, including fluoro, chloro and bromo radicals, such as methyl-p-benzoquinone, 2,3-dichloro-5,6-dicyano-p-benzoquinone, tetrachloro-p-benzoquinone (chloranil), tetrafluoro-p-benzoquinone, tetramethyl-p-benzoquinone, 2,5-diphenyl-p-benzoquinone, and tetrachloro-o-benzoquinone (o-chloranil). It has been found that quinones having an oxidation-reduction potential below about 0.4 volt, e.g. 9, 10-anthraquinone and tetrahydroxy-p-benzoquinone, will not produce HNS when reacted with HNB.

As shown in the reaction scheme above, one mole of benzoquinone or equivalent is theoretically required per mole of HNB in the process of the present invention. Generally a molar excess of the quinone over the HNB is employed to ensure maximum yields of HNS. Significantly, lower yields of HNS are obtained when the amount of quinone is reduced significantly below one mole per mole of HNB.

The solvent employed should be capable of dissolving the reactants and promoting the dehydrogenation of HNB to HNS with a quinone according to the process of the present invention. In general, suitable solvents include those having average beta values within the range of about 0.75 to 1.0 on the beta-scale of solvent hydrogen bond acceptor (HBA) basicities according to page 382, Table III of the article by M. J. Kamlet and R. W. Taft in J. Am. Chem. Soc. 98, 377 (1976). Examples of such solvents include hexamethylphosphoric triamide (HMPT), dimethyl sulfoxide (DMSO), and 1-methyl-2-pyrrolidinone, of which HMPT is preferred. Such solvents are viewed as proton acceptors strong enough to induce the formation of an incipient carbanion of HNB, thus facilitating the removal of hydrogen by the quinone. Solvents having average beta values below those noted above, e.g. dimethylformamide (DMF) and tetrahydrofuran (THF), are not effective for promoting the dehydrogenation of HNB. However, the latter solvents, e.g. DMF, are effective for promoting the dehydrogenation of HMB to HNS with quinones and hence constitute suitable reaction solvents, providing they dissolve the reactants, do not produce unwanted side reactions, and have suitable boiling points, when employed in combination with an organic amine having a pKa value within the range of about 4.5 to about 6.5, such as pyridine, aniline, N,N-dimethylaniline, 2- and 4-picolines and quinoline. Also, by employing an organic amine of pKa of about 4.5 to 6.5 in mixture with a solvent having an average beta value between 0.75 and 1.0 (defined above), the yield of HNS obtained according to the present process may be further increased over that obtained in the absence of such an amine.

After the introduction of the reagents, the mixture is heated while being stirred to accomplish the dehydrogenation of the HNB. The reaction is accomplished at temperatures of about 50° C. to 110° C. and preferably about 65° C. to 90° C. The reaction will proceed, although more slowly, at still lower temperatures. To increase the degree of completion of the reaction, the mixture is heated for about 1 to about 5 hours and preferably from 0.5 to 3 hours. However, excessive heating periods in the presence of an added base such as pyridine will decrease the yield of HNS. It is believed that the reason for this is that the HNS will form by-products via competing side reactions in the presence of such bases when subjected to excessive heating.

The HNS is then recovered from the reaction mixture in accordance with procedures well known to those skilled in the art. For example, the reaction mixture can be diluted with water and the solid precipitate filtered from the mixture. The precipitate can then be extracted with acetone to dissolve impurities and the insoluble HNS filtered from the acetone solution of impurities and dried.

The following examples will more fully illustrate the embodiments of the invention. Unless otherwise specified, all parts and percentages are by weight.

EXAMPLE I 1.2 grams (0.0027 mole) of 2,2′,4,4′,6,6′-hexanitrobibenzyl (HNB) and 1.5 grams (0.0061 mole) of chloranil (tetrachloro-p-benzoquinone) are mixed in 15 mls of hexamethyl phosphoric triamide (HMPT). This mixture is heated for 3 hours at a temperature of 70° C. while stirring. The reaction mixture is then diluted with water and the solid precipitate filtered from the mixture. The precipitate is then dried to give 2.4 grams of solids. The dried solids are then extracted with acetone. The acetone insoluble HNS is separated by filtration and dried to yield 1.05 grams (87% of theoretical) of a grey insoluble solid having a melting point of 315° C. and identified as 2,2′,4,4′,6,6′-hexanitrostilbene (HNS) as determined by infrared spectrum.

The above example was repeated four times with an average yield of 80% of theoretical.

EXAMPLE II 1.2 grams (0.0027 mole) of HNB and 0.57 gram (0.0053 mole) of p-benzoquinone are mixed in 15 mls of HMPT. The mixture is heated for 3 hours at a temperature of 70° C. while stirring. The reaction mixture is then diluted with water and the solid precipitate is filtered from the mixture. The precipitate is then extracted with acetone, and the acetone insoluble HNS is separated by filtration and dried to yield 0.93 gram (78% of theoretical) of HNS as determined by infrared spectrum.

EXAMPLE III 1.2 grams (0.0027 mole) of HNB and 1.31 grams (0.0053 mole) of tetrachloro-o-benzoquinone (ortho-chloranil) are mixed in 15 mls of HMPT. The mixture is heated for 3 hours at a temperature of 70° C. while stirring. The reaction mixture is then diluted with water and the solid precipitate filtered from the mixture. The precipitate is then purified by extraction with acetone and dried as described in Example I to yield 1.00 gram (83% of theoretical) of HNS as determined by infrared spectrum.

EXAMPLE IV 1.2 grams (0.0027 mole) of HNB and 0.84 gram (0.0053 mole) of 1,4-naphthoquinone are mixed in 15 mls of HMPT. The mixture is heated for 3 hours at a temperature of 70° C. while stirring. The reaction mixture is then diluted with water and the solid precipitate is filtered from the mixture. The precipitate is then purified by extraction with acetone and dried to yield 0.85 gram (71% of theoretical) of HNS.

EXAMPLE V 1.2 grams (0.0027 mole) of HNB and 1.20 grams (0.0053 mole) of 2,3-dichloro-5,6-dicyano-p-benzoquinone are mixed in 15 mls of HMPT. The mixture is heated for 3 hours at a temperature of 70° C. while stirring. The reaction mixture is then diluted with water and the solid precipitate is filtered from the mixture. The precipitate is then purified by extraction with acetone and dried to yield 1.07 grams (89% of theoretical) of HNS.

EXAMPLE VI

Example I is repeated but 9,10-anthraquinone is used in place of chloranil. The process produced no HNS.

EXAMPLE VII

Example II is repeated but the solvent N,N-dimethylformamide (DMF) is used in place of HMPT. The process produced no HNS.

EXAMPLE VIII 1.2 grams (0.0027 mole) of HNB and 0.57 gram (0.0053 mole) of p-benzoquinone are mixed in 15 mls of dimethyl sulfoxide (DMSO). The mixture is heated for 3 hours at a temperature of 70° C. while stirring. The reaction mixture is then diluted with water and the solid precipitate is filtered from the mixture. The precipitate is then purified by extraction with acetone and dried to yield 0.22 gram (18% of theoretical) of HNS.

EXAMPLE IX

Example VIII is repeated except that the mixture is heated for 3 hours at a temperature of 95° C. while stirring. The yield is 0.39 gram (33% of theoretical) of HNS.

EXAMPLE X 1.2 grams (0.0027 mole) of HNB and 0.57 gram (0.0053 mole) of p-benzoquinone are mixed in 15 mls of 1-methyl-2-pyrrolidinone. The mixture is heated for 3 hours at a temperature of 70° C. while stirring. The reaction mixture is then diluted with water and the solid precipitate is filtered from the mixture. The precipitate is then extracted with acetone and dried to yield 0.27 gram (23% of theoretical) of HNS.

EXAMPLE XI

Example II is repeated except the solvent orthodichlorobenzene is substituted for HMPT and the mixture is heated for 3 hours at 150° C. The process produced no HNS.

EXAMPLE XII 0.45 gram (0.001 mole) of HNB and 0.50 gram (0.002 mole) of orthochloranil are mixed in 50 mls of tetrahydrofuran. The mixture is heated at reflux (65° C.) for 3 hours while stirring. The process produced no HNS.

EXAMPLE XIII 0.90 gram (0.002 mole) of HNB and 0.50 gram (0.002 mole) of chloranil are mixed in 50 mls of xylene. The mixture is heated at reflux (130° C.) for 2 hours while stirring. The process produced no HNS.

EXAMPLE XIV 1.2 grams (0.0027 mole) of HNB, 0.57 gram (0.0053 mole) of p-benzoquinone and 0.5 gram (0.0063 mole) of pyridine are mixed in 15 mls of DMF. The mixture is heated for 3 hours at 70° C. while stirring. The mixture is then diluted with water and the precipitated solid is filtered from the mixture. The precipitate is then extracted with acetone and dried to yield 0.76 gram (63% of theoretical) of HNS.

EXAMPLE XV

Example XIV is repeated except the mixture is heated for 5 hours instead of 3 hours. The yield of HNS is 0.61 gram (51% of theoretical).

EXAMPLE XVI 1.2 grams (0.0027 mole) of HNB, 0.57 gram (0.0053 mole) of p-benzoquinone and 1.0 gram (0.0126 mole) of pyridine are mixed in 15 mls of DMF. The mixture is heated for 3 hours at 70° C. while stirring. The mixture is then diluted with water and the precipitated solid is filtered from the mixture. The precipitate is then extracted with acetone and dried to yield 0.66 gram (55% of theoretical) of HNS.

EXAMPLE XVII

Example XIV is repeated except 0.25 gram (0.0032 mole) of pyridine is used. The yield of HNS is 0.78 gram (65% of theoretical).

EXAMPLE XVIII 1.2 grams (0.0027 mole) of HNB, 0.57 gram (0.0053 mole) of p-benzoquinone and 0.25 gram (0.0032 mole) of pyridine are mixed in 15 mls of DMF. The mixture is heated at 70° C. for 1½ hours. The mixture is then diluted with water and the precipitated solid is filtered from the mixture. The precipitate is then extracted with acetone and dried to yield 0.89 gram (74% of theoretical) of HNS.

EXAMPLE XIX

Example XVII is repeated except DMSO is used in place of DMF. The yield of HNS is 0.84 gram (70% of theoretical).

EXAMPLES XX–XXII

In accordance with the procedure set forth in Example I, the following quinones are mixed with HNB in the solvent HMPT. The mixture is heated for 3 hours at 70° C. The molar ratio of quinone to HNB is 2.

| Quinone | HNS % Yield |
|---|---|
| 2,5-diphenylbenzoquinone | 70% |
| Methyl-p-benzoquinone | 72% |
| tetramethyl-p-benzoquinone | 46% |

EXAMPLES XXIII–XXVII

In accordance with the procedure set forth in Example XIV, p-benzoquinone, HNB and the following organic bases are mixed in the solvent DMF. The mixture is heated for 3 hours at 70° C. The molar ratio of benzoquinone to HNB is 2 and the molar ratio of base to HNB is 1.2.

| Base | HNS % Yield |
|---|---|
| Aniline | 53% |
| Quinoline | 73% |
| N,N-DiMethylaniline | 21% |
| 2-Picoline | 68% |
| 4-Picoline | 70% |

This invention has been described with respect to certain preferred embodiments and various modifications. Variations in the light thereof will be suggested to persons skilled in the art and are to be included within the spirit and purview of this application and the scope of the appended claims.

What is claimed is:

1. A process for preparing 2,2',4,4',6,6'-hexanitrostilbene comprising the steps of mixing 2,2',4,4',6,6'-hexanitrobibenzyl and a quinone having an oxidation-reduction potential of from about 0.4 volt to about 1.0 volt in a reaction solvent at a temperature of about 50° C. to about 110° C., and then recovering the hexanitrostilbene from the reacted mixture, said reaction solvent being capable of promoting a dehydrogenation reaction with said 2,2',4,4',6,6'-hexanitrobibenzyl.

2. A process as defined in claim 1 wherein said reaction takes place at temperatures of about 65° C. to about 90° C.

3. A process as defined in claim 1 wherein the quinone is selected from the group consisting of o-benzoquinone, p-benzoquinone, 1,2-napthoquinone, 1,4-napthoquinone and substitution products thereof containing at least one substitute radical selected from the group consisting of methyl, phenyl, cyano and halogen.

4. A process as defined in claim 1 wherein the reaction solvent is selected from the group consisting of hexamethyl phosphoric triamide, dimethyl sulfoxide and 1-methyl-2-pyrrolidinone.

5. A process as defined in claim 1 or claim 2 wherein the reaction solvent is hexamethyl phosphoric triamide.

6. A process as defined in claim 1 wherein the reaction solvent includes an organic amine having a pKa value of about 4.5 to about 6.5.

7. A process as defined in claim 6 wherein the organic amine is selected from the group consisting of aniline, quinoline, N,N-dimethylaniline, pyridine, 2-picoline and 4-picoline.

8. A process as defined in claim 1, wherein the reaction solvent has an average beta value of 0.75 to 1.0 on the beta scale of solvent hydrogen bond acceptor basicities.

9. A process as defined in claim 2 wherein the mixture is heated for about 1.5 hours to about 3 hours.

10. A process as defined in claim 8 wherein the quinone is selected from the group consisting of 2,3-dichloro-5,6-dicyano-p-benzoquinone, tetrafluoro-p-benzoquinone, tetrachloro-o-benzoquinone, tetrachloro-p-benzoquinone, p-benzoquinone, 2,5-diphenyl-benzoquinone, methyl-p-benzoquinone, 1,4-napthoquinone, and tetramethyl-p-benzoquinone.

* * * * *